United States Patent [19]

Costin

[11] 4,139,459
[45] Feb. 13, 1979

[54] QUINOLIZINIUM ANION EXCHANGE RESINS AND MONOMERS AND METHODS FOR MAKING THEM

[75] Inventor: Charles R. Costin, Jenkintown, Pa.

[73] Assignee: Rohm and Haas Company, Philadelphia, Pa.

[21] Appl. No.: 808,938

[22] Filed: Jun. 22, 1977

Related U.S. Application Data

[62] Division of Ser. No. 550,493, Feb. 18, 1975, Pat. No. 4,046,766.

[51] Int. Cl.$^2$ ............... C08F 26/00; B01D 15/04; C08F 8/28
[52] U.S. Cl. ................. 210/37 R; 526/23; 526/46; 526/54; 526/259; 526/923
[58] Field of Search .............. 260/2.1 E; 526/23, 259, 526/258; 210/24 R, 37 R

[56] References Cited

U.S. PATENT DOCUMENTS

| 3,794,584 | 2/1974 | Kunin | 210/24 |
| 4,018,676 | 4/1977 | Hoffsommer et al. | 210/24 |

Primary Examiner—Joseph L. Schofer
Assistant Examiner—Peter F. Kulkosky
Attorney, Agent, or Firm—Louis F. Kline, Jr.

[57] ABSTRACT

Quinolizinium resins may be produced by quaternizing substituted vinyl pyridine polymers followed by subjecting the resulting product to a condensation reaction to obtain quinolizinium functionality. The resins are useful as ion exchange resins, adsorbents and catalysts.

8 Claims, No Drawings

QUINOLIZINIUM ANION EXCHANGE RESINS AND MONOMERS AND METHODS FOR MAKING THEM

This application is a division of my U.S. Pat. application Ser. No. 550,493 filed Feb. 18, 1975, now U.S. Pat. No. 4,046,766, granted Sept. 6, 1977.

This invention relates to quinolizinium condensation products of quaternized vinyl pyridine polymers. More particularly the invention concerns methods of preparation and application of such quinolizinium products as thermally stable resins in catalytic reaction, as additives in the polymer industry or as adsorbents in the pollution field.

Certain quinolizinium type compounds have been described in the prior art, particularly those useful in the pharmaceutical applications. For example, British patent No. 916,507 describes a condensation process for the production of dehydroquinolizinium compounds. Functionalized quinolizinium monomer and polymers however appear not to have been previously considered. The present invention deals with such functionalized quinolizinium resins, modes of preparation and application.

According to the present invention, useful resins may be prepared by quaternizing substituted vinyl pyridine polymers and condensing the resulting product to quinolizinium resins. The resulting polymers have surprisingly high thermal stability and additionally have been discovered to possess excellent physical stability, good regeneration efficiency — particularly for the strong base resins, and increased total anion exchange capacity. The resins have the further advantage in that they are prepared by a method considered safer than the usual chloromethylation technique.

The resins of the invention may be macroreticular in nature which macroreticularity is achieved by well known processes as disclosed in British patents Nos. 932,125 and 932,126; and U.S. Pat. Nos. 3,275,548 and 3,357,158. Alternatively, the resins may be gelular in nature.

Although the quinolizinium resins of the invention may have the structure involving many aromatic rings, a preferred structure and general synthesis is illustrated by the following reaction.

Reaction I

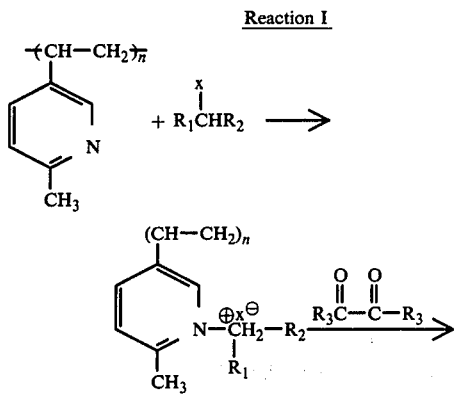

-continued
Reaction I

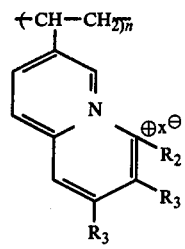

where $R_1$ is any activating group and may be alkoxy carbonyl or cyano;
where $R_2$ and $R_3$ are hydrogen, lower alkyl, phenyl, substituted lower alkyl, alkoxy or cyano groups
where $R_1$, $R_2$ and $R_3$ may be the same or different
where x is hydroxyl or halogen
More preferred values for $R_1$ are cyano and carboxyl.
More preferred values for $R_2$ are lower alkyl and hydrogen.

Vinyl pyridine polymers which may be used as starting compounds may be prepared by a variety of well known polymerization techniques, although suspension polymerization is preferred.

The quaternization reaction of the polymer to the intermediate functionalized vinyl pyridine is also well known in the art. A preferred reactant for the applicant's resins is ethyl bromoacetate.

Quaternizing reaction conditions usually include temperatures of from about room temperature to reflux temperature under normal atmospheric pressure.

It is advantageous to use as starting compounds vinyl pyridine polymers which have utilized a comonomer such as divinyl pyridine or trimethylol propane trimethacrylate during polymerization. Such comonomers, often called crosslinkers, aid in achieving a strong bead formation. Any utility which requires beads possessing strong physical stability should preferably contain an adequate percentage of crosslinker. Utilities which do not require such strong physical stability may utilize resins which are only lightly or not at all crosslinked. For example, applications requiring the ion exchange resin or catalyst in powdered form may use lightly crosslinked beads. The condensing reaction takes place in the presence of a α-dicarbonyl compound preferably glyoxal or diacetyl.

The condensation reaction conditions may vary widely although preferred conditions generally include reaction temperatures of 70–110° C. preferably 75–90° C. This temperature is of course dependent on the pressures present during the reaction. Preferably however the reaction is carried out at atmospheric pressures, although super atmospheric pressures up to about 2 or 3 atmospheres might prove to be advantageous in lowering reaction times. The reagents during either quaternization or following condensation reaction should be present in an amount of at least one equivalent. Condensation reactions are more preferably run at temperatures of around 78° C.

Another preferred method of preparation involves the intermediate formation of a functionalized quinolizinium monomer. The starting compound preferably is vinyl pyridine which is quaternized by a standard reactant to provide a product which may by a condensation reaction cause the formation of the functionalized monomer which subsequently may be polymerized to the resin.

A specific reaction scheme illustrating this method is shown below

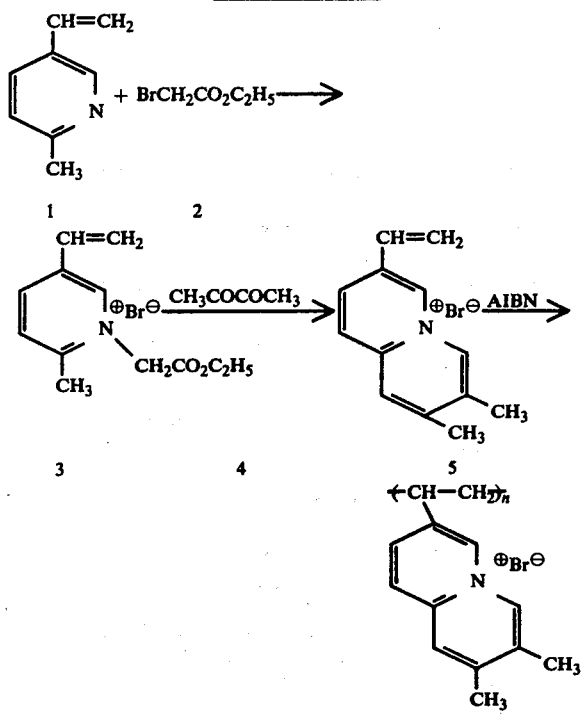

Reaction II

It should be understood that an analogous latitude applies as to the range of amounts and nature of reactants and reaction conditions which pertain to the synthesis illustrated by Reaction I. Similarly, the substituent groups may also vary. The above reactions I and II illustrate that the resins of the inventor may be obtained by starting with a polymeric vinyl pyridine or by a formed functionalized quinolizinium monomer. It will be noted that in Formula 5 the vinyl group, $-CH=CH_2$, is bonded directly to a quinolizinium ring carbon atom.

Specific resins prepared according to the process of the invention are shown in Table I.

400 available from the Rohm and Haas Company for strong base capacity at 140° C. The comparative thermal stability is determined by the following test.

The resin as received is converted completely to the hydroxide form using approximately 1000 mls. of 1 N NaOH for 15 mls. of resin. The resin is rinsed with D. I. water and placed in an appropriate container containing excess D. I. water (at least a 20 to 1 water to resin ratio) and the container is placed in an oven of appropriate temperature (140° C.). Periodically, the sample is removed, completely converted to the HCl form and evaluated for solids content, and true strong base capacity. After this, the resin is reconverted to the hydroxide form using 1 N-HCl followed by 1 N-NaOH and replaced in the same temperature environment. Several checks may be made at all temperatures to confirm that the resins are completely in the hydroxide form during the testing periods. The results indicate that the quinolizinium resins have consistently greater thermal stability than the comparative resins. For examle, quinolizinium ion Resin A retained essentially all its true strong base capacity after 6.5 days at 140° C. vs. almost total destruction of the control resin Amberlite IRA-400 (93% loss of true strong base capacity and 50% loss of volume). The results are shown in the following table

|  | Solids | ABC (meq/g) | TSB (meq/g) |
|---|---|---|---|
| Resin A | 37.20 | 3.95 | 1.91 |
| Resin A (140°,6.5 days) | 40.11 | 3.89 | 1.77 |
| IRA-400 | 52.14 | 4.09 | 4.09 |
| IRA-400 (140°,6.5 days) | 68.95 | 2.20 | 0.28 |

Physical stability is measured as a Chatillon value. The Chatillon test measures the force required to fracture a resin bead when placed between two parallel plates, and receives its name from the apparatus used to determine this friability or fragmentation force. Its purpose is to simulate the frictional and pressure forces exerted on individual resin beads in actual use.

These specifications generally include testing at least sixty, water saturated, 20–30 mesh, resin beads. The average force required to fracture individual beads of anion resin in the hydroxide form or cation resin in the hydrogen form given as a number of grams per bead is termed the Chatillon Value.

The resins of the invention when compared to com-

Table I

| Intermediate Substituents of Reaction I | | Quinolizinium Resin | | | | |
|---|---|---|---|---|---|---|
| $R_1$ | $R_2$ | Name | $R_2$ | $R_3$ | AEC meq/g dry | TSB meq/g dry |
| $CO_2CH_3$ | H | Poly-2,3-dimethyl-7-vinyl quinolizinium Ion | H | $CH_3$ | 3.95 | 1.91 |
| $CO_2CH_3$ | H | Poly-3-vinylquinolizinium Ion | H | H | 4.96 | 0.93 |
| $CO_2CH_3$ | $C_6H_5$ | Poly-2,3-dimethyl-4-phenyl-7-vinylquinolizinium Ion | $C_6H_5$ | $CH_3$ | 2.93 | 1.08 |
| $CO_2CH_3$ | $CH_3$ | Poly-2,3,4-trimethyl-7-vinyl-quinolizinium Ion | $CH_3$ | $CH_3$ | 3.70 | 1.76 |
| H | CN | Poly-2,3-dimethyl-4-cyano-7-vinylquinolizinium Ion | CN | $CH_3$ | 3.51 | 1.70 |
| $CO_2CH_3$ | $C_6H_5$ | Poly-4-phenyl-7-vinyl-quinolizinium Ion | $C_6H_5$ | H | 3.53 | 0.50 |
| $CO_2CH_3$ | $CH_3$ | Poly-4-methyl-7-vinyl-quinolizinium Ion | $CH_3$ | H | 4.63 | 0.79 |
| H | CN | Poly-4-cyano-7-vinylquinolizinium Ion | CN | H | 4.38 | 0.70 |

As mentioned hereinbefore, the resins of the invention have been tested for thermal stability and physical stability. Resin A as described hereinafter was tested against a commercial resin identified as Amberlite IRAmercial resins for their physical stability show results as indicated in the following Table II.

Table II

| Resin | Chatillon Value |
|---|---|
| Resin A, Macroreticular | 1,098 g/bead |
| IRA-900, Macroreticular | 300 g/bead |
| IRA-400, Gelular | 50 g/bead |
| Resin A, Gelular | 355 g/bead |

As indicated hereinbefore, the resins are useful in a variety of applications. These applications utilizing the ion exchange characteristics, the adsorption characteristics and thermal stability include hot condensate flushing, purification processes of primary coolant loops in nuclear reactant systems and waste stream purifications whether such streams are aqueous or gaseous in nature.

The following examples serve to illustrate the invention further.

EXAMPLE I

A. Preparation of Poly-2-methyl-5-vinylpyridine-7% Divinylbenzene (Reaction I)

| Charges (3 mole scale) | |
|---|---|
| Aqueous Phase | Organic Phase |
| 960 g Water | 51 g Divinylbenzene (80%) |
| 390 g Sodium Chloride | 525 g 2-Methyl-5-vinylpyridine |
| 45 g Primafloc C-3 | 309 g Diisobutyl Ketone |
| 6 g Primafloc C-7 | 5.7 g Azo-bis-isobutyronitrile |
| 0.3 g Sodium Nitrite | |

The aqueous phase is added to a 3-liter flask fitted with a constant-torque stirrer, condenser, thermometer, and a nitrogen inlet-outlet system. The stirring rate is adjusted to 148 rpm. After adding the organic phase, the depth of the four-prong stirrer is adjusted to obtain the ideal suspension. The system is flushed with nitrogen and a constant sweep of nitrogen is maintained throughout the reaction period. The mixture is heated to 65° C. and maintained at this temperature for 20 hours. Triton CR-32 (15 drops), a foam inhibitor, is added to minimize foaming and the solution is heated to reflux. The solvents are azeotroped until no visible organic solvent distills. The resin is filtered, washed with water, and dried in a vacuum at 50° C. overnight. The resulting weak base resin has the following properties:

| | |
|---|---|
| Anion Exchange Capacity (meq/g) | 7.11 |
| Solids (%) | 40.80 |
| Surface Area (m²/g) | 32.76 |
| Porosity (cc/cc) | 0.32 |

B. Preparation of Poly-2-methyl-5-vinylpyridine-N-carboethoxy Bromide (Reaction I)

Charges 30.0 g (0.18 equiv.) Macroreticular poly-2-methyl-5-vinylpyridine of Example I (A) (7% divinylbenzene)
32.0 g (0.19 mole) Ethyl Bromoacetate
230 ml Methanol The dried poly-2-methyl-5-vinylpyridine and 200 ml of the methanol are placed in a 1-liter flask equipped with a stirrer, thermometer, and condenser. The beads are allowed to swell for 30 minutes at 65° C. with agitation. After the swelling period the excess methanol is removed by filtration. The ethyl bromoacetate dissolved in 20 ml of the methanol is added to the swollen beads at room temperature (ca. 25° C.). Additional methanol (10 ml) is used to wash the last trace of reagent into the reaction flask. The reaction mixture is stirred at room temperature for 30 minutes, reflux temperature (60–65° C.) for 4 hours, and for an additional 15–16 hours at room temperature. The resin is filtered, washed twice with methanol, and column washed with two bed volumes of methanol. Drying the resin in a vacuum oven at 50° C. for 2 hours gives 61.9 g of yellow beads.

C. Preparation of the Quinolizinium Ion Resin - Resin A

Charges 31.0 g (0.09 equiv) Poly-2-methyl-5-vinylpyridine-N-carboethoxy Bromide of Example I (B)
9.0 g (0.105 mole) 2,3-Butanedione
13.0 g (0.101 mole) Di-n-butylamine
230 ml 2B (ethanol) Alcohol The dried poly-2-methyl-5-vinylpyridine-N-carboethoxy bromide and 200 ml of the 2B alcohol are added to a flask equipped with a stirrer, thermometer, condenser, and gas inlet and outlet tubes. The apparatus is swept with nitrogen and a slow sweep of this gas is maintained during the reaction period. The beads are allowed to swell at reflux temperature (78° C.) for 30 minutes with stirring. The excess solvent is removed by filtration. At room temperature, the 2,3-butanedione and di-n-butylamine are added followed by 30 ml of 2B alcohol. The reaction mixture is heated to reflux (78° C.) and maintained at this temperature for 4 hours. The black beads are filtered while warm (50° C.) and washed with 3 × 80 ml portions of warm (50° C.) 2B alcohol, then transferred to a column and washed with methanol (1 pint). Drying the resin in a vacuum oven at 50° C. for two hours gives 30.4 g of product in the bromide form. The resulting Resin A has the following properties:

| | |
|---|---|
| Total Anion Exchange Capacity (meq/g) | 3.95 |
| True Strong Base Capacity (meq/g) | 1.91 |
| Solids % | 37.20 |
| Apparent Density (g/cc) | 0.855 |
| True Density (g/cc) | 1.095 |
| Surface Area (m²/g) | 85.0 |
| Porosity (cc/cc) | 0.309 |

EXAMPLE II

Charges 10.0 g (0.035 equiv) Poly-2-methyl-5-vinylpyridine-N-carboethoxy bromide of Example I (B)
5.5 g (0.038 mole) 40% aqueous glyoxal
7.8 g (0.076 mole) sodium bisulfite
9.6 g (0.11 mole) sodium bicarbonate Using the apparatus and nitrogen system described in Example 1, the intermediate 2 and 100 ml of deionized water are heated at 90° C. for 1 hour. The excess water is removed by filtration and the resin is cooled to 40–50° C. The sodium bicarbonate dissolved in 30 ml of deionized water was added to the swollen beads while maintaining the temperature at 40–50° C. A warm (60° C) solution of the glyoxal and the sodium bisulfite in 50 ml of deionized water is added. The temperature is increased to 80° C. and maintained at this temperature for ten hours. Following the reaction period, the resin is filtered while warm (80° C.), washed with three bed volumes of methanol. Drying the resins at 50° C. in a vacuum oven for two hours gives 6.7 g of dark amber beads. The resulting Resin B, characterized in that the R substituent as referred to in Resin I is hydrogen, has the following properties:

| | |
|---|---|
| Total Anion Exchange Capacity (meq/g) | 4.96 |
| True Strong Base Capacity (meq/g) | 0.93 |
| Solids (%) | 30.00 |

EXAMPLE III

1. Preparation of 2,3-Dimethyl-7-vinylquinolizinium bromide following Reaction II Charges
Reaction A
 17.8 g (0.15 mole) 2-methyl-5-vinylpyridine
 25.0 g (0.15 mole) Ethyl Bromoacetate
 0.5 g Benzoquinone
 150 ml Ethanol
Reaction B
 12.9 g (0.15 mole) 2,3-Butanedione (Diacetyl)
 19.7 g (0.15 mole) Di-n-butylamine
Reactions A and B are carried out in the same flask without the isolation of the intermediate.

The 2-methyl-5-vinylpyridine, benzoquinone, and ethanol are charged to a 500 ml flask equipped with a stirrer, thermometer, and condenser. The ethyl bromoacetate is added and the dark solution is stirred at room temperature for 16 hours. The 2,3-butanedione and di-n-butylamine are added to the solution at room temperature. The reaction mixture is heated to reflux (78° C.) and maintained at this temperature for one hour. Cooling the mixture to 0° C. produced 9.1 g (23%) of vacuum dried intermediate monomer as an off-white powder.

The quinolizinium resin monomer has the following properties: mp 204° C. (decomposition); ir (nujol) 1615(d) cm$^{-1}$; nmr (D$_2$O) δ 2.55 (3H,s); 2.62 (3H,s), 5.77 and 6.17 (2H,m), 6.9 (1H,m), 8.1 (3H,m) and 8.75 (2H,s).

EXAMPLE IV

Preparation of Poly-2,3-dimethyl-7-vinylquinolizinium Ion following Reaction II Charges
 1.6 g (0.006 mole) 2,3-Dimethyl-7-vinylquinolizinium Bromide intermediate monomer
 0.08 g Azo-bis-isobutyronitrile
 10 ml Ethanol
 0.25 g Divinylbenzene (80%)

The reactants are placed in a 50 ml flask containing a nitrogen inlet-outlet system. The system is flushed with nitrogen and a constant nitrogen sweep is maintained throughout the reaction period. The mixture is heated to 65° C. and held at this temperature for 18 hours. The dark amber polymer is washed with acetone and vacuum dried (50° C.) to give 1.13 g of quinolizinium polymer (Br form). The polymer is ground to a fine particle size and converted to the chloride form using 7% hydrochloric acid.

| | |
|---|---|
| Solids (%) | 12.19 |
| Anion Exchange Capacity (meq/g dry) | 5.49 |
| True Strong Base (meq/g dry) | 3.83 |

EXAMPLE V

Silica Removal

The quinolizinium ion resin efficiently removes silica in a column operation using an 8 lb. regeneration level and 2 gpm/ft$^3$ flow rate. As shown in the following table, Resin A with a strong base capacity measuring 47% of the SBC of IRA-400, removes silica with a column capacity equal to 58% of IRA-400.

| Resin | True Strong Base (meq/g) | Regeneration Level (a) (lb NaOH/ft$^3$) | Silica Capacity (b,c) (Kilograins/ft$^3$) |
|---|---|---|---|
| IRA-400 | 4.0 | 8 | 16.8 |
| IRA-400 | 4.0 | 20 | 22.0 |
| Resin A | 1.7 | 8 | 9.7 |
| Resin A | 1.7 | 20 | 9.9 |

(a) Room temperature regeneration
(b) Determined at 1 ppm silica leakage.
(c) Influent contained 200 ppm HCl and 19 ppm SiO$_2$

I claim:
 1. A vinyl quinolizinium anion exchange resin polymer produced by quaternizing substituted vinyl pyridine polymer or polymerizing a prefunctionalized vinyl quinolizinium monomer in which the vinyl group, —CH=CH$_2$, is bonded directly to a quinolizinium ring carbon atom, in either case optionally including a crosslinking comonomer in the polymerization.
 2. The anion exchange resin polymer of claim 1 in which the polymer has the following formula:

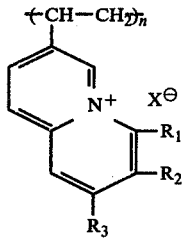

wherein R$_1$, R$_2$, and R$_3$ are independently selected from hydrogen, lower alkyl phenyl, substituted lower alkyl, alkoxy and cyano and X is a negative counterion.
 3. The anion exchange resin of claim 2 wherein R$_1$ = H, R$_2$ and R$_3$ = CH$_3$ and X is Br$^-$.
 4. The anion exchange resin of claim 2 wherein R$_1$, R$_2$, and R$_3$ are hydrogen.
 5. The anion exchange resin of claim 2 wherein R$_1$ = CH$_3$ and R$_2$ and R$_3$ = hydrogen.
 6. The anion exchange resin of claim 2 wherein R$_1$ = CN and R$_2$ and R$_3$ are hydrogen.
 7. A method of preparing a quinolizinium resin which comprises quaternizing with a compound of the formula:

A substituted vinyl pyridine polymer and subjecting the resulting product to a condensation reaction with a compound of the formula:

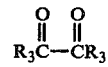

to obtain the resin having quinolizinium functionality, where R$_1$ is any activating group and may be alkoxy, carbonyl or cyano; where R$_2$ and R$_3$ are hydrogen, lower alkyl, phenyl, substituted lower alkyl, alkoxy or cyano groups; where R$_1$, R$_2$ and R$_3$ may be the same or different; and where x is hydroxyl or halogen.
 8. An adsorption process which comprises using the quinolizinium polymeric composition of claim 1 as an adsorbent for silica from a liquid mixture comprising the same.

* * * * *